(12) United States Patent
Zahradnik et al.

(10) Patent No.: US 7,094,551 B2
(45) Date of Patent: Aug. 22, 2006

(54) IMMUNOASSAYS, ASSAY METHODS, ANTIBODIES AND METHOD OF CREATING ANTIBODIES FOR DETECTING FGF-23

(76) Inventors: Richard J. Zahradnik, 33142 Acapulco Dr., Dana Point, CA (US) 92673; Jeffrey Lavigne, 31881 Via Flores, San Juan Capistrano, CA (US) 92675; Harald Jueppner, 59 Kinnaird St., Cambridge, MA (US) 02139

( * ) Notice: Subject to any disclaimer, the term of this patent is extended or adjusted under 35 U.S.C. 154(b) by 716 days.

(21) Appl. No.: 10/245,141

(22) Filed: Sep. 17, 2002

(65) Prior Publication Data

US 2005/0106755 A1    May 19, 2005

(51) Int. Cl.
*G01N 33/53*    (2006.01)
*G01N 33/543*   (2006.01)

(52) U.S. Cl. ................ 435/7.1; 435/7.5; 435/7.94; 436/518; 436/815

(58) Field of Classification Search ............ 435/7.1, 435/7.5, 7.94; 436/518, 815
See application file for complete search history.

(56) References Cited

U.S. PATENT DOCUMENTS

| 4,376,110    A * | 3/1983 | David et al. ............ 435/5 |
| 2005/0106755 A1* | 5/2005 | Zahradnik et al. ....... 436/518 |

FOREIGN PATENT DOCUMENTS

| WO | 0161007 | 8/2001 |
| WO | 0166595 | 9/2001 |
| WO | 0208271 | 1/2002 |
| WO | 0214504 | 2/2002 |

OTHER PUBLICATIONS

Lederman et al, Molecular Immunology, vol. 28, No. 11, pp. 1171-1181, 1991.*
Pharis Biotec Grants Exclusive Patent License to Nichols Institute Diagnostics for Method of Detecting Active Parathyroid Hormone, Dec. 13, 2001, Print Out from Web Site, home-investing.excite.com/news/pr/011212/nichols-granted-lic.

* cited by examiner

*Primary Examiner*—David Saunders
(74) *Attorney, Agent, or Firm*—Stetina Brunda Garred & Brucker

(57) ABSTRACT

Immunoassays, assay methods, antibodies and methods of producing antibodies for the detection of fibroblast growth factor-23 (FGF-23). The immunoassay and assay method preferably comprise a non-competitive, sandwich-type assay utilizing a first bound antibody having affinity to a first site of the FGF-23 molecule, and a second, labeled antibody having an affinity for a second site present upon the FGF-23 molecule. The antibodies and methods of generating the same include administering antigenic peptide fragments of the FGF-23 molecule, monitoring the antibody titre produced thereby, extracting and selecting antibodies from the antisera having a specificity for the desired antigenic region of FGF-23, and purifying same. The antibodies may be incorporated into the immunoassay of the present invention or utilized for a variety of assay-type purposes for the detection of FGF-23.

10 Claims, 8 Drawing Sheets

HUMAN FIBROBLAST GROWTH FACTOR-23 PEPTIDE SEQUENCES

```
Met Leu Gly Ala Arg Leu Arg Leu Trp Val Cys Ala Leu Cys Ser Val
Cys Ser Met Ser Val Leu Arg Ala Tyr Pro Asn Ala Ser Pro Leu Leu
Gly Ser Ser Trp Gly Gly Leu Ile His Leu Tyr Thr Ala Thr Ala Arg
Asn Ser Tyr His Leu Gln Ile His Lys Asn Gly His Val Asp Gly Ala
Pro His Gln Thr Ile Tyr Ser Ala Leu Met Ile Arg Ser Glu Asp Ala
Gly Phe Val Val Ile Thr Gly Val Met Ser Arg Arg Tyr Leu Cys Met
Asp Phe Arg Gly Asn Ile Phe Gly Ser His Tyr Phe Asp Pro Glu Asn
Cys Arg Phe Gln His Gln Thr Leu Glu Asn Gly Tyr Asp Val Tyr His
Ser Pro Gln Tyr His Phe Leu Val Ser Leu Gly Arg Ala Lys Arg Ala
Phe Leu Pro Gly Met Asn Pro Pro Pro Tyr Ser Gln Phe Leu Ser Arg
Arg Asn Glu Ile Pro Leu Ile His Phe Asn Thr Pro Ile Pro Arg Arg
His Thr Arg Ser Ala Glu Asp Asp Ser Glu Arg Asp Pro Leu Asn Val
Leu Lys Pro Arg Ala Arg Met Thr Pro Ala Pro Ala Ser Cys Ser Gln
Glu Leu Pro Ser Ala Glu Asp Asn Ser Pro Met Ala Ser Asp Pro Leu
Gly Val Val Arg Gly Gly Arg Val Asn Thr His Ala Gly Gly Thr Gly
Pro Glu Gly Cys Arg Pro Phe Ala Lys Phe Ile
```

Figure 1 (SEQ. ID NO. 1)

MOUSE FIBROBLAST GROWTH FACTOR-23 PEPTIDE SEQUENCES

```
Met Leu Gly Thr Cys Leu Arg Leu Leu Val Gly Val Leu Cys Thr Val
Cys Ser Leu Gly Thr Ala Arg Ala Tyr Pro Asp Thr Ser Pro Leu Leu
Gly Ser Asn Trp Gly Ser Leu Thr His Leu Tyr Thr Ala Thr Ala Arg
Thr Ser Tyr His Leu Gln Ile His Arg Asp Gly His Val Asp Gly Thr
Pro His Gln Thr Ile Tyr Ser Ala Leu Met Ile Thr Ser Glu Asp Ala
Gly Ser Val Val Ile Thr Gly Ala Met Thr Arg Arg Phe Leu Cys Met
Asp Leu His Gly Asn Ile Phe Gly Ser Leu His Phe Ser Pro Glu Asn
Cys Lys Phe Arg Gln Trp Thr Leu Glu Asn Gly Tyr Asp Val Tyr Leu
Ser Gln Lys His His Tyr Leu Val Ser Leu Gly Arg Ala Lys Arg Ile
Phe Gln Pro Gly Thr Asn Pro Pro Phe Ser Gln Phe Leu Ala Arg
Arg Asn Glu Val Pro Leu Leu His Phe Tyr Thr Val Arg Pro Arg Arg
His Thr Arg Ser Ala Glu Asp Pro Pro Glu Arg Asp Pro Leu Asn Val
Leu Lys Pro Arg Pro Arg Ala Thr Pro Val Pro Val Ser Cys Ser Arg
Glu Leu Pro Ser Ala Glu Glu Gly Gly Pro Ala Ala Ser Asp Pro Leu
Gly Val Leu Arg Arg Gly Arg Gly Asp Ala Arg Gly Gly Ala Gly Gly
Ala Asp Arg Cys Arg Pro Phe Pro Arg Phe Val
```

Figure 1a (SEQ. ID NO. 2)

```
Tyr Pro Asn Ala Ser Pro Leu Leu Gly Ser Ser Trp Gly Gly Leu Ile
His Leu Tyr Thr Ala Thr Ala Arg Asn Ser Tyr His Leu Gln Ile His
Lys Asn Gly His Val Asp Gly Ala Pro His Gln Thr Ile Tyr Ser Ala
Leu Met Ile Arg Ser Glu Asp Ala Gly Phe Val Val Ile Thr Gly Val
Met Ser Arg Arg Tyr Leu Cys Met Asp Phe Arg Gly Asn Ile Phe Gly
Ser His Tyr Phe Asp Pro Glu Asn Cys Arg Phe Gln His Gln Thr Leu
Glu Asn Gly Tyr Asp Val Tyr His Ser Pro Gln Tyr His Phe Leu Val
Ser Leu Gly Arg Ala Lys Arg Ala Phe Leu Pro Gly Met Asn Pro Pro
Pro Tyr Ser Gln Phe Leu Ser Arg Arg Asn Glu Ile Pro Leu Ile His
Phe Asn Thr Pro Ile Pro Arg Arg His Thr Arg Ser Ala Glu Asp Asp
Ser Glu Arg Asp Pro Leu Asn Val Leu Lys Pro Arg Ala Arg Met Thr
Pro Ala Pro Ala Ser Cys Ser Gln Glu Leu Pro Ser Ala Glu Asp Asn
Ser Pro Met Ala Ser Asp Pro Leu Gly Val Val Arg Gly Gly Arg Val
Asn Thr His Ala Gly Gly Thr Gly Pro Glu Gly Cys Arg Pro Phe Ala
Lys Phe Ile
```
Figure 6 (25-251) (SEQ. ID NO. 3)

```
Tyr Pro Asn Ala Ser Pro Leu Leu Gly Ser Ser Trp Gly Gly Leu Ile
His Leu
```
Figure 7 (25-42) (SEQ. ID NO. 4)

```
Tyr Pro Asn Ala Ser Pro Leu Leu Gly Ser Ser Trp Gly Gly Leu Ile
His Leu Tyr Thr Ala Thr Ala Arg Asn Ser Tyr His Leu Gln Ile His
Lys Asn Gly His Val Asp Gly Ala Pro His Gln Thr Ile
```
Figure 8 (25-69) (SEQ. ID NO. 5)

```
Tyr Pro Asn Ala Ser Pro Leu Leu Gly Ser Ser Trp Gly Gly Leu Ile
His Leu Tyr Thr Ala Thr Ala Arg Asn Ser Tyr His Leu Gln Ile His
Lys Asn Gly His Val Asp Gly Ala Pro His Gln Thr Ile Tyr Ser Ala
Leu Met Ile Arg Ser Glu Asp Ala Gly Phe Val Val Ile Thr Gly Val
Met Ser Arg Arg Tyr Leu Cys Met Asp Phe Arg Gly
```
Figure 9 (25-100) (SEQ. ID NO. 6)

```
Tyr Pro Asn Ala Ser Pro Leu Leu Gly Ser Ser Trp Gly Gly Leu Ile
His Leu Tyr Thr Ala Thr Ala Arg Asn Ser Tyr His Leu Gln Ile His
Lys Asn Gly His Val Asp Gly Ala Pro His Gln Thr Ile Tyr Ser Ala
Leu Met Ile Arg Ser Glu Asp Ala Gly Phe Val Val Ile Thr Gly Val
Met Ser Arg Arg Tyr Leu Cys Met Asp Phe Arg Gly Asn Ile Phe Gly
Ser His Tyr Phe Asp Pro Glu Asn Cys Arg Phe Gln His Gln Thr Leu
Glu Asn Gly Tyr Asp Val Tyr His Ser Pro Gln Tyr His Phe Leu Val
Ser Leu Gly Arg Ala Lys Arg Ala Phe Leu Pro Gly Met Asn Pro Pro
Pro Tyr Ser Gln Phe Leu Ser Arg Arg Asn Glu Ile Pro Leu Ile His
Phe Asn Thr Pro Ile Pro
```
Figure 10 (25-174) (SEQ. ID NO. 7)

His Leu Tyr Thr Ala Thr Ala Arg Asn Ser Tyr His Leu Gln Ile His

Figure 11 (41-56) (SEQ. ID NO. 8)

Tyr His Leu Gln Ile His Lys Asn Gly His Val Asp Gly Ala Pro His Gln Thr Ile

Figure 12 (51-69) (SEQ. ID NO. 9)

Asn Gly His Val Asp Gly Ala Pro His Gln Thr Ile Tyr Ser Ala Leu Met Ile Arg Ser Glu Asp Ala Gly

Figure 13 (58-81) (SEQ. ID NO. 10)

Pro His Gln Thr Ile Tyr Ser Ala Leu Met Ile Arg Ser Glu Asp Ala Gly

Figure 14 (65-81) (SEQ. ID NO. 11)

Tyr Ser Ala Leu Met Ile Arg Ser Glu Asp Ala Gly Phe Val Val Ile

Figure 15 (70-85) (SEQ. ID NO. 12)

Val Ile Thr Gly Val Met Ser Arg Arg Tyr Leu Cys Met Asp Phe Arg Gly

Figure 16 (84-100) (SEQ. ID NO.13)

Ser Arg Arg Tyr Leu Cys Met Asp Phe Arg Gly Asn Ile Phe Gly Ser His Tyr Phe Asp Pro Glu Asn Cys Arg Phe

Figure 17 (90-115) (SEQ. ID NO. 14)

Gly Asn Ile Phe Gly Ser His Tyr Phe Asp Pro Glu Asn Cys Arg Phe Gln His Gln Thr Leu

Figure 18 (100-120) (SEQ. ID NO. 15)

Pro Glu Asn Cys Arg Phe Gln His Gln Thr Leu Glu Asn Gly Tyr Asp Val Tyr His Ser Pro

Figure 19 (110-130) (SEQ. ID NO. 16)

Thr Leu Glu Asn Gly Tyr Asp Val Tyr His Ser

Figure 20 (119-129) (SEQ. ID NO. 17)

```
Pro Gln Tyr His Phe Leu Val Ser Leu Gly Arg Ala Lys Arg Ala Phe
Leu Pro Gly Met Asn
```
Figure 21 (130-150) (SEQ. ID NO. 18)

```
Arg Ala Lys Arg Ala Phe Leu Pro Gly Met Asn Pro Pro Tyr Ser
Gln Phe Leu Ser Arg
```
Figure 22 (140-160) (SEQ. ID NO.19)

```
Asn Pro Pro Pro Tyr Ser Gln Phe Leu Ser Arg Arg Asn Glu Ile Pro
Leu Ile His Phe Asn
```
Figure 23 (150-170) (SEQ. ID NO. 20)

```
Arg Arg Asn Glu Ile Pro Leu Ile His Phe Asn Thr Pro Ile Pro
```
Figure 24 (160-174) (SEQ. ID NO. 21)

```
Ser Ala Glu Asp Asp Ser Glu Arg Asp Pro Leu Asn Val Leu Lys Pro
Arg Ala Arg Met Thr Pro Ala Pro Ala Ser Cys Ser Gln Glu Leu Pro
Ser Ala Glu Asp Asn Ser Pro Met Ala Ser Asp Pro Leu Gly Val Val
Arg Gly Gly Arg Val Asn Thr His Ala Gly Gly Thr Gly Pro Glu Gly
Cys Arg Pro Phe Ala Lys Phe Ile
```
Figure 25 (180-251) (SEQ. ID NO. 22)

```
Ser Ala Glu Asp Asp Ser Glu Arg Asp Pro Leu Asn Val Leu Lys Pro
Arg Ala Arg Met Thr Pro Ala Pro Ala Ser Cys
```
Figure 26 (180-206) (SEQ. ID NO. 23)

```
Glu Arg Asp Pro Leu Asn Val Leu Lys Pro Arg Ala Arg Met Thr Pro
Ala Pro Ala Ser Cys
```
Figure 27 (186-206) (SEQ. ID NO. 24)

```
Glu Arg Asp Pro Leu Asn Val Leu Lys Pro Arg Ala Arg Met Thr Pro
Ala Pro Ala Ser Cys Ser Gln Glu Leu Pro Ser Ala Glu Asp Asn Ser
Pro Met Ala Ser Asp Pro Leu Gly Val Val Arg Gly Gly Arg Val Asn
Thr His Ala Gly Gly Thr Gly Pro Glu Gly Cys
```
Figure 28 (186-244) (SEQ. ID NO. 25)

```
Cys Ser Gln Glu Leu Pro Ser Ala Glu Asp Asn Ser Pro Met Ala Ser
Asp
```
Figure 29 (206-222) (SEQ. ID NO. 26)

```
Cys Ser Gln Glu Leu Pro Ser Ala Glu Asp Asn Ser Pro Met Ala Ser
Asp Pro Leu Gly Val Val Arg Gly Gly Arg Val Asn Thr His Ala Gly
Gly Thr Gly Pro Glu Gly Cys
```
Figure 30 (206-244) (SEQ. ID NO. 27)

```
Gly Val Val Arg Gly Gly Arg Val Asn Thr His Ala Gly Gly Thr Gly
Pro Glu Gly Cys
```
Figure 31 (225-244) (SEQ. ID NO. 28)

```
Gly Val Val Arg Gly Gly Arg Val Asn Thr His Ala Gly Gly Thr Gly
Pro Glu Gly Cys Arg Pro Phe Ala Lys Phe Ile
```
Figure 32 (225-251) (SEQ. ID NO. 29)

```
Gly Arg Val Asn Thr His Ala Gly Gly Thr Gly Pro Glu Gly Cys Arg
Pro Phe Ala Lys Phe Ile
```
Figure 33 (230-251) (SEQ. ID NO. 30)

```
Gly Pro Glu Gly Cys Arg Pro Phe Ala Lys Phe Ile
```
Figure 34 (240-251) (SEQ. ID NO. 31)

IMMUNOASSAYS, ASSAY METHODS, ANTIBODIES AND METHOD OF CREATING ANTIBODIES FOR DETECTING FGF-23

STATEMENT RE: FEDERALLY SPONSORED RESEARCH/DEVELOPMENT

This invention was supported in part by a grant made by the United States government, and the United States government may have certain rights in the invention.

CROSS-REFERENCE TO RELATED APPLICATIONS (NA)

BACKGROUND OF THE INVENTION

There has recently been substantial interest in fibroblast growth factors (FGF's), their biological activity, and their association with certain diseases. Of most interest include FGF-23, a 251-amino acid protein which, in humans, has the amino acid sequence as set forth in SEQ ID NO. 1 and in mice has the amino acid sequence set forth in SEQ ID No. 2. Exemplary of the teachings and publications discussing FGF-23 include Patent Cooperation Treaty International Publication No. WO 01/61007 A2, entitled *Fibroblast Growth Factor-23 Molecules and Uses Thereof* published on Aug. 23, 2001, and Patent Cooperation Treaty International Publication No. WO 01/66595 A2, entitled *Human FGF-23 Gene and Gene Expression Products,* published on Sep. 13, 2001, the teachings of both are expressly incorporated herein by reference.

In this regard, currently available data appears to suggest that FGF-23 is either directly or indirectly involved in the regulation of phosphate homeostasis. Moreover, FGF-23 appears to be associated with certain renal phosphate wasting disorders leading to hypophosphatemia, which are among the more significant causes of defective mineralization of bone and growth plate development. For example, patients with autosomal dominant hypophosphatemic rickets (ADHR), a rare genetic disorder, carry one of several FGF-23 mutations that make the protein resistant to proteolytic cleavage. Additionally, tumors that cause oncogenic osteomalacia (OOM) have been shown to over-express FGF-23 mRNA, which is likely attributable to the elevated concentrations of FGF-23 in the blood that consequently causes renal phosphate wasting in this group of patients.

As a result, the measurement of FGF-23, particularly with respect to concentrations in blood circulation, is likely to provide an important indication of the body's ability to regulate phosphate homeostasis, and will further likely serve as an important diagnostic tool for the laboratory evaluation of patients with a variety of different hypophosphatemic disorders. With respect to the latter, it is contemplated that the measurement of human FGF-23 will be particularly important in evaluating disorders such as oncogenic osteomalacia, X-linked hypophosphatemic rickets, and autosomal dominant hypophosphatemic rickets.

Unfortunately, however, there is not yet available an assay capable of qualitatively and quantitatively indicating the presence of FGF-23 within a fluid specimen, much less an immunoassay and assay method that is relatively inexpensive, relatively easy to manufacture, and possesses desired sensitivity and reproducibility necessary for use of such immunoassay and assay method for diagnostic applications.

BRIEF SUMMARY OF THE INVENTION

The present invention specifically addresses and alleviates the above-identified deficiencies in the art. In this regard, the present invention is directed to an immunoassay and assay method which are capable of determining the presence and concentration of FGF-23 in a fluid specimen. According to the preferred embodiment, the immunoassay and assay method comprise a non-competitive, sandwich-type assay, which detects the presence of FGF-23 by binding two receptors, namely antibodies at two separate discrete sites of the FGF-23 protein molecule. In such arrangement, the first antibody or capture antibody has an affinity for a first site present on the FGF-23 molecule and is bound to or subsequently prepared for binding by a solid phase such that when FGF-23 molecules are present, such molecules become affixed in position thereto. Thereafter, a second antibody or detection antibody is introduced having an affinity for the second, dissimilar site upon the FGF-23 molecule. The second antibody further includes a label coupled therewith, which may take the form of any of a variety known in the art, including a radioactive, fluorescent, enzymatic, dye or other detectable moiety.

Preferably, the first and second antibodies will have affinities for separate, discrete sequences of amino acids encompassed within the FGF-23 molecules that are preferably present at discrete, spatially distinct regions of the FGF-23 molecule. Specifically, the first and second antibodies incorporated into the immunoassay and the assay method of the present invention will have an affinity for polypeptide fragments that are at least about 70% identical to the intact FGF-23 molecule, as well as the polypeptides as set forth in SEQ ID NOS. 3 through 31. In one preferred embodiment, the first and second antibodies will have a specificity for those amino acid sequences set forth in SEQ ID NOS. 26 and 28. In another preferred embodiment for the detection of the intact FGF-23 molecule, the first antibody will have an affinity for the amino acid sequence set forth at SEQ ID NO. 24 and the second antibody will have a specificity for the amino acid sequences set forth at either SEQ ID NO. 9 and/or SEQ ID NO. 4. In yet a further preferred embodiment of the present invention, the first antibody will have a specificity to a sequence set forth at SEQ ID NO. 28 and the second antibody will have a specificity for the amino acid set forth at SEQ ID NO. 24. It will be understood, however, that in any embodiment the first and second antibodies will have affinities for non-identical sequences.

The present invention further includes antibodies and methods of producing antibodies that have a specificity for polypeptides having the aforementioned sequences. With respect to the method of producing such antibodies, such method preferably comprises the steps of administering a peptide which is at least 70% identical to the polypeptides set forth in a respective one of the peptides as set forth in SEQ ID NOS. 1 through 31 to a host animal. In a preferred method, the host animal comprises a goat (although numerous other species known in the art can be utilized).

Following the administration of such antigen, the antibody titre produced thereby is then monitored. Antisera produced in the host animal is isolated and selected such that the antibodies thereof have a specificity for the desired polypeptide sequence, and thereafter isolated and purified. Such antibodies may then be labeled or otherwise incorporated into the assay of the present invention, or utilized for any other possible application involving the isolation and/or identification of FGF-23.

It is therefore an object of the present invention to provide an immunoassay and assay method for readily and accurately determining the presence of FGF-23 in a fluid specimen.

Another object of the present invention is to provide an immunoassay and assay method for determining the presence of FGF-23 that can be utilized to determine the regulation of bone and mineral homeostasis, as well as be utilized as a diagnostic tool for the laboratory evaluation of patients having a variety of hypophosphatemic disorders.

Another object of the present invention is to provide antibodies and methods of producing antibodies that have an affinity for FGF-23 and are capable of binding to FGF-23 on at least two or more sites of the molecule thereof to thus enable two or more antibodies to be simultaneously bound thereto.

Another object of the present invention is to provide antibodies and a method of producing antibodies that have an affinity for FGF-23 that can be readily utilized for the detection of FGF-23 in humans, as well as possibly other species.

Still further objects of the present invention are to provide an immunoassay, assay method, antigens, and methods of producing antigens that can be constructed and/or practiced utilizing conventional, commercially-available technology, are relatively inexpensive, and are capable of producing rapid, accurate, reliable and reproducible results.

BRIEF DESCRIPTION OF THE DRAWINGS

An illustrative and presently preferred embodiment of the invention is shown in the accompanying drawings in which:

FIG. 1 illustrates the amino acid sequence of human FGF-23 (SEQ ID NO.:1);

FIG. 1a: illustrates the amino acid sequence of mouse FGF-23 (SEQ ID NO.:2);

FIG. 6 illustrates an amino acid sequence corresponding to amino acid residues 25–251 of human FGF-23 (SEQ ID NO.: 3).

FIG. 7 illustrates an amino acid sequence corresponding to amino acid residues 25–42 of human FGF-23 (SEQ ID NO.: 4).

FIG. 8 illustrates an amino acid sequence corresponding to amino acid residues 25–69 of human FGF-23 (SEQ ID NO.: 5).

FIG. 9 illustrates an amino acid sequence corresponding to amino acid residues 25–100 of human FGF-23 (SEQ ID NO.: 6).

FIG. 10 illustrates an amino acid sequence corresponding to amino acid residues 25–174 of human FGF-23 (SEQ ID NO.: 7).

FIG. 11 illustrates an amino acid sequence corresponding to amino acid residues 41–56 of human FGF-23 (SEQ ID NO.: 8).

FIG. 12 illustrates an amino acid sequence corresponding to amino acid residues 51–69 of human FGF-23 (SEQ ID NO.: 9).

FIG. 13 illustrates an amino acid sequence corresponding to amino acid residues 58–81 of human FGF-23 (SEQ ID NO.: 10).

FIG. 14 illustrates an amino acid sequence corresponding to amino acid residues 65–81 of human FGF-23 (SEQ ID NO.: 11).

FIG. 15 illustrates an amino acid sequence corresponding to amino acid residues 70–85 of human FGF-23 (SEQ ID NO.: 12).

FIG. 16 illustrates an amino acid sequence corresponding to amino acid residues 84–100 of human FGF-23 (SEQ ID NO.: 13).

FIG. 17 illustrates an amino acid sequence corresponding to amino acid residues 90–115 of human FGF-23 (SEQ ID NO.: 14).

FIG. 18 illustrates an amino acid sequence corresponding to amino acid residues 100–120 of human FGF-23 (SEQ ID NO.: 15).

FIG. 19 illustrates an amino acid sequence corresponding to amino acid residues 110–130 of human FGF-23 (SEQ ID NO.: 16).

FIG. 20 illustrates an amino acid sequence corresponding to amino acid residues 119–129 of human FGF-23 (SEQ ID NO.: 17).

FIG. 21 illustrates an amino acid sequence corresponding to amino acid residues 130–150 of human FGF-23 (SEQ ID NO.: 18).

FIG. 22 illustrates an amino acid sequence corresponding to amino acid residues 140–160 of human FGF-23 (SEQ ID NO.: 19).

FIG. 23 illustrates an amino acid sequence corresponding to amino acid residues 150–170 of human FGF-23 (SEQ ID NO.: 20).

FIG. 24 illustrates an amino acid sequence corresponding to amino acid residues 160–174 of human FGF-23 (SEQ ID NO.: 21).

FIG. 25 illustrates an amino acid sequence corresponding to amino acid residues 180–251 of human FGF-23 (SEQ ID NO.: 22).

FIG. 26 illustrates an amino acid sequence corresponding to amino acid residues 180–206 of human FGF-23 (SEQ ID NO.: 23).

FIG. 27 illustrates an amino acid sequence corresponding to amino acid residues 186–206 of human FGF-23 (SEQ ID NO.: 24).

FIG. 28 illustrates an amino acid sequence corresponding to amino acid residues 186–244 of human FGF-23 (SEQ ID NO.: 25).

FIG. 29 illustrates an amino acid sequence corresponding to amino acid residues 206–222 of human FGF-23 (SEQ ID NO.: 26).

FIG. 30 illustrates an amino acid sequence corresponding to amino acid residues 206–244 of human FGF-23 (SEQ ID NO.: 27).

FIG. 31 illustrates an amino acid sequence corresponding to amino acid residues 225–244 of human FGF-23 (SEQ ID NO.: 28).

FIG. 32 illustrates an amino acid sequence corresponding to amino acid residues 225–251 of human FGF-23 (SEQ ID NO.: 29).

FIG. 33 illustrates an amino acid sequence corresponding to amino acid residues 230–251 of human FGF-23 (SEQ ID NO.: 30).

FIG. 34 illustrates an amino acid sequence corresponding to amino acid residues 240–251 of human FGF-23 (SEQ ID NO.: 31).

DETAILED DESCRIPTION OF THE INVENTION

Figure 2:
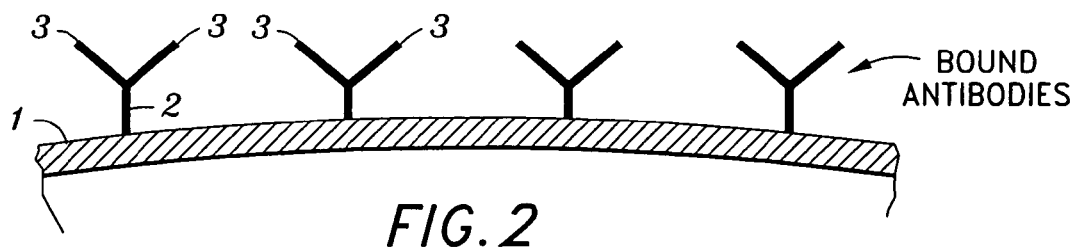
FIG. 2 is a side-view of an immunoassay incorporating a bound antibody, the latter having an affinity for a first site upon the FGF-23 molecule.

The detailed description set forth below is intended as a description of the presently preferred embodiment of the invention, and is not intended to represent the only form in which the present invention may be constructed or utilized. The description sets forth the functions and sequences of steps for constructing and operating the invention. It is to be understood, however, that the same or equivalent functions and sequences may be accomplished by different embodiments and that they are also intended to be encompassed within the scope of the invention.

The present invention encompasses immunoassays, assay methods, antibodies and methods of producing antibodies that are designed to have a specificity or affinity to a variety of antigenic regions of the FGF-23 polypeptide for both humans and a variety of other species, such as mice.

For purposes of the present invention, the term "FGF-23" refers to a polypeptide comprising the amino acid sequence set forth in FIG. 1, SEQ ID NO.: 1, and related polypeptides. Similarly, the term "FGF-23 polypeptide fragment" or "peptide antigen" will refer to antigenic sequences of amino acids formed upon FGF-23 corresponding to amino acid residues 25–251 of FGF-23 (SEQ ID NO. 3); amino acid residues 25–42 of FGF-23 (SEQ ID NO. 4); amino acid residues 25–69 of FGF-23 (SEQ ID NO. 5); amino acid residues 25–100 of FGF-23 (SEQ ID NO. 6); amino acid residues 25–174 of FGF-23 (SEQ ID NO. 7); amino acid residues 41–56 of FGF-23 (SEQ ID NO. 8); amino acid residues 51–69 of FGF-23 (SEQ ID NO. 9); amino acid residues 58–81 of FGF-23 (SEQ ID NO. 10); amino acid residues 65–81 of FGF-23 (SEQ ID NO. 11); amino acid residues 70–85 of FGF-23 (SEQ ID NO. 12); amino acid residues 84–100 of FGF-23 (SEQ ID NO. 13); amino acid residues 90–115 of FGF-23 (SEQ ID NO. 14); amino acid residues 100–120 of FGF-23 (SEQ ID NO. 15); amino acid residues 110–130 of FGF-23 (SEQ ID NO. 16); amino acid residues 119–129 of FGF-23 (SEQ ID NO. 17); amino acid residues 130–150 of FGF-23 (SEQ ID NO. 18); amino acid residues 140–160 of FGF-23 (SEQ ID NO. 19); amino acid residues 150–170 of FGF-23 (SEQ ID NO. 20); amino acid residues 160–174 of FGF-23 (SEQ ID NO. 21); amino acid residues 180–251 of FGF-23 (SEQ ID NO. 22); amino acid residues 180–206 of FGF-23 (SEQ ID NO. 23); amino acid residues 186–206 of FGF-23 (SEQ ID NO. 24); amino acid residues 186–244 of FGF-23 (SEQ ID NO. 25); amino acid residues 206–222 of FGF-23 (SEQ ID NO. 26); amino acid residues 206–244 of FGF-23 (SEQ ID NO. 27); amino acid residues 225–244 of FGF-23 (SEQ ID NO. 28); amino acid residues 225–251 of FGF-23 (SEQ ID NO. 29); amino acid residues 230–251 of FGF-23 (SEQ ID NO. 30); and amino acid residues 240–251 of FGF-23 (SEQ ID NO. 31) of the intact human FGF-23 molecule. Furthermore, with respect to those FGF-23 polypeptide fragments incorporating amino acid residues 25–35, and in particular amino acid residues 27–29 (i.e., SEQ ID NOS. 3–7), one or more of such amino acid residues may be glycosylated to more closely mimic certain naturally derived fragments, discussed more fully below.

As additionally used herein, the term "identity" refers to a relationship between the sequences of two or more polypeptide molecules and is directed to the degree of sequence relatedness between amino acids present in the respective polypeptides as determined by the match of two or more amino acid sequences. For purposes of the present application, "identity" is directed to the percentage of same residues between two sequences, consistent with the definition of "identity" and "sequence identity" set forth in Patent Cooperation Treaty International Publication No. WO 01/61007 A2, entitled *Fibroblast Growth Factor-23 Molecules and Uses Thereof* published on Aug. 23, 2001, and Patent Cooperation Treaty International Publication No. WO 01/66595 A2, entitled *Human FGF-23 Gene and Gene Expression Products*, published on Sep. 13, 2001, the teachings of each of which are expressly incorporated herein by reference.

Figure 3:
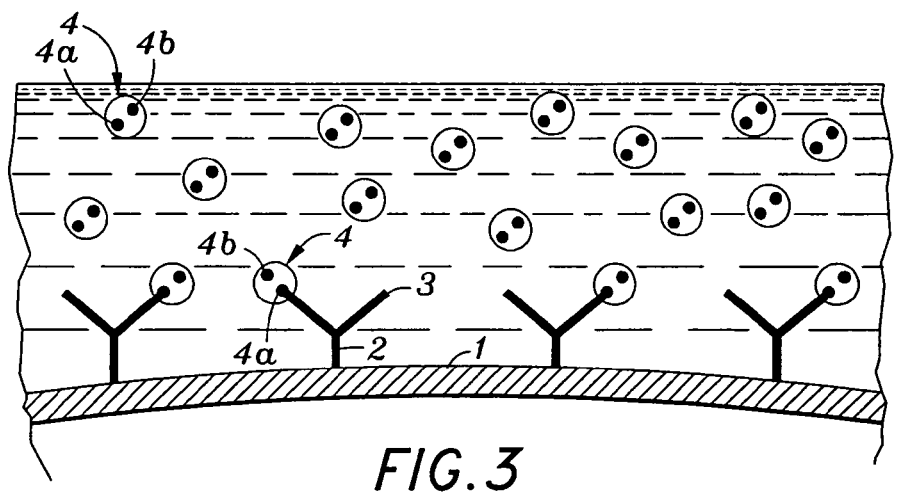
FIG. 3 is a side-view of the assay of FIG. 2 depicting the introduction of a fluid sample to such assay having molecules of FGF-23 present therein, a portion of the molecules bound to the immobilized antibody.
Figure 4:
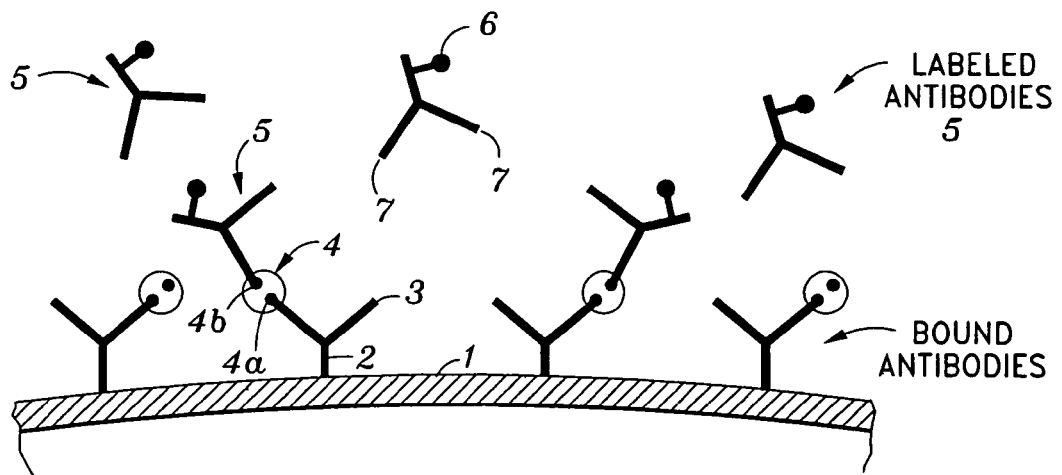
FIG. 4 is a side-view of the assay depicted in FIGS. 2 and 3 showing a second antibody having a label affixed thereto, said second antibody having an affinity for a second site upon the FGF-23 molecule.

With reference to FIGS. 2–4, there is depicted an immunoassay constructed in accordance with the preferred embodiment of the present invention. As illustrated, there is provided a well or backing 1 upon which are bound a first antibody 2. As will be appreciated by those skilled in the art, first antibody or capture antibody 2 may be immobilized or conjugated for immobilization upon backing 1 via any of a variety of conventional techniques known in the art. First antibody 2 further includes an antibody binding site 3 that has an affinity to bind with a specific site present upon the FGF-23 molecule, discussed more fully below. In this respect, the first antibody 2 will be raised and affinity purified to have a known specificity for a known, selectively-chosen antigenic region present upon the FGF-23 molecule.

In use, the capture antibodies 2 bound to backing 1 will be subjected to a fluid sample suspected of having FGF-23 protein molecules present therein, as shown in FIG. 3. In this respect, such fluid sample may take any variety of biological samples, including but not limited to serum, plasma or cell culture media.

Once subjected to the capture antibodies, the antigen binding site 3 thereof will bind to a first antigenic site 4a for a presentation upon the FGF-23 protein molecule 4, as shown. As per conventional sandwich-type assays, the FGF-23 protein molecules become bound to the first capture antibody 2, which cause the same to remain in fixed position.

Simultaneously with first or capture antibody 2 above or thereafter, as depicted in FIG. 4, a second antibody 5 having a label 6 attached thereto is introduced to the assay. The second antibody 5 will have an antigen binding site 7 specific to a second antigenic region 4(b) of the FGF-23 protein molecule 4.

According to the preferred embodiments of the present invention, as presently contemplated, the binding site of the first antibody 2 will have a specificity for those amino acid sequences set forth in FIG. 27 (SEQ ID NO. 24 (186–206)), FIG. 29 (SEQ ID NO. 26 (206–222)), or FIG. 31 (SEQ ID NO. 28 (225–244)), whereas the binding site of the second antibody will have a specificity for those amino acid sequences set forth in FIG. 7 (SEQ ID NO. 4 (25–42)), FIG. 12 (SEQ ID NO. 9 (51–69)), FIG. 27 (SEQ ID NO. 24 (186–206)), FIG. 29 (SEQ ID NO. 26 (206–222)), or FIG. 31 (SEQ ID NO. 28 (225–244)).

As will be appreciated, the specificity of the first antibody will be dissimilar to the specificity of the second antibody such that in use, the first and second antibodies are capable of sequentially and simultaneously binding to an intact molecule of the FGF-23. Along these lines, it is believed that in the most highly preferred embodiment presently known, first antibody 2 will have a specificity for the amino acid sequence set forth in FIG. 27 (SEQ ID NO. 24 (186–206)) whereas the second antibody will have a specificity for either sequence set forth in FIG. 12 (SEQ ID NO.9 (51–69)) and/or FIG. 7 (SEQ ID NO. 4 (25–42)). In an alternative most highly preferred embodiment, first antibody 2 will have a specificity for the amino acid sequence set forth in FIG. 31 (SEQ ID NO. 28 (225–244) and second antibody will have a specificity for the amino acid sequence set forth in FIG. 27 (SEQ ID NO. 24 (186–206)).

As will further be appreciated by those skilled in the art, the label 6 attached to second antibody 5, provided to detect the presence of FGF-23, may comprise any detectable moiety known in the art, including but not limited to, radioactive, fluorescent, enzymatic or dye-type tracers. According to one preferred embodiment, the label 6 comprises biotin to which horseradish peroxidase (HRP) conjugated to avidin will bind for detection. In such applications, the enzymatic activity of the antibody complex bound to the backing 1 is measured utilizing conventional methods, such as through spectrophotometric analysis as compared to a standardized reference. Along these lines, any of a variety of prior art practices may be utilized to determine the presence and concentration of immobilized FGF-23 detected through the immunoassays and assay methods of the present invention.

As will further be appreciated, in order to insure the integrity of the results produced by the immunoassays and assay methods of the present invention, there may optionally be provided a control receptor or antibody (not shown) formed upon the backing 1 having a specific affinity for an unrelated control ligand. Alternatively, bound receptors 2 known to have FGF-23 molecules attached thereto may be utilized as a control reference per conventional techniques known in the art. In this regard, the immunoassay and assay methods of the present invention will preferably take the form of those immunoassays produced by Immutopics, Inc., of San Clemente, Calif., and in particular, its human FGF-23 C-Terminal enzyme-linked immunosorbent assay (ELISA) kit utilized for the determination of human fibroblast growth factor 23 levels in serum, plasma or cell culture media, 96 test kit, catalogue No. 60-6000.

Figure 5:
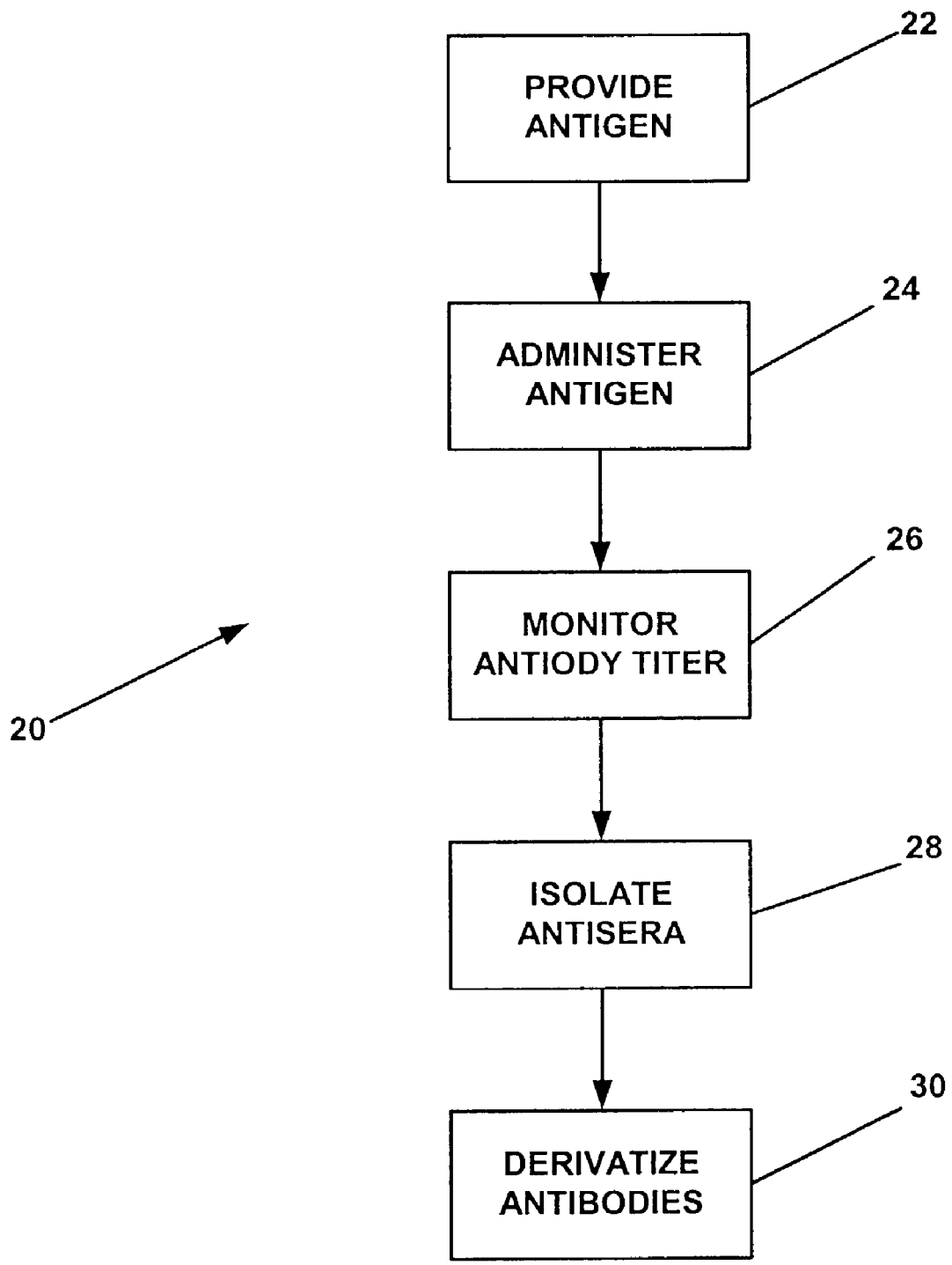
FIG. 5 is a flow chart depicting the steps for producing antibodies according to a preferred embodiment of the present invention.

In addition to the immunoassay and assay methods provided above, the present invention further is directed to antibodies and methods of producing antibodies that are directed to separate and discrete antigenic regions of the FGF-23 protein molecule. To that end, there is illustrated in FIG. 5 the method 20 for generating such antibodies.

In the first step 22, there is provided an antigenic peptide that is at least 70% identical to those peptides identified in FIGS. 1, 1a and 6–34 as SEQ ID NO. 1–31, respectively. It will likewise be recognized that such antigenic peptides will additionally comprise all functional derivatives of those set forth in SEQ ID NOS. 1–31, and will expressly include all functionally comparable peptides derived from the same regions of FGF-23, as reflected in SEQ ID NOS. 1–31, and having a similar ability to induce antibodies specific for those distinct antigenic regions present upon the FGF-23 protein molecule.

As will be appreciated by those skilled in the art, those functional derivatives may be similarly positioned peptides or peptides derived from SEQ ID NOS. 1–31, having substitutions, additions or deletions of amino acids, provided the derivation does not alter the ability of the peptide antigen to induce antibodies reactive to FGF-23. Along these lines, desired amino acid substitutions can be determined by those skilled in the art such that suitable variance of those polypeptides set forth at SEQ ID NOS. 1–31 can be derived using well-known techniques. It should further be recognized that the peptide antigens of the present invention include those peptides whose amino acid sequences may be shifted within a few amino acids upstream or downstream of the antigen peptides reflected in SEQ ID NOS 1–31, as well as those peptides having conservative amino acid changes such that substitutions, additions or deletions of amino acids or changes do not significantly affect the ability of the peptide antigen to induce antibodies with high affinity and specificity for those respective amino acid sequences of FGF-23, as reflected in SEQ ID NOS. 1–31. Moreover, as discussed above, to the extent intact FGF-23 or any peptide derived therefrom that includes amino acid residues 25–35, and in particular 27–29 (i.e., SEQ ID NOS. 1–7), one or more of such specified amino acids may be glycosylated in order to better reflect its naturally-occurring state. Accordingly, such additions, deletions or modifications of those sequences of amino acids incorporated as part of FGF-23 are expressly considered to fall within the scope of the present invention.

As to the production of such antigenic peptides, the same may be made by any of a variety of techniques well-known in the art. For example, such peptides may be synthesized by conventional methods, such as solid-phase chemical synthesis or by recombinant technology. It will additionally be appreciated that the antigenic peptides of the present invention may optionally be chemically coupled to a carrier protein. Alternatively, recombinant peptides may be generated as fusion proteins to increase antigenicity once administered to the host animal, as discussed more fully below.

Once derived, the peptide antigen is administered in step 24 to a host animal, preferably in combination with an adjuvant. It is contemplated that a variety of species may be utilized as suitable subjects for prompting the sought after immune response. To achieve that end, the antigens may be administered to the subject via any of a variety of methods, such as subcutaneous or intramuscular injection, for example. As will be appreciated, the dose of peptide antigen administered will correspondingly vary with the specific peptide antigen utilized, as well as the host animal.

Once administered, the results of antibody titres produced in the host animal are monitored in step 26, which may be conducted through any of a variety of techniques known in the art, such as routine bleeds and the like. Thereafter, antisera is isolated 28 and thereafter screened for the presence of antibody having a binding affinity therefor. Along these lines, it will be recognized by those skilled in the art that such antibodies may be monoclonal or polyclonal in nature. To that end, it is preferred that the antisera derived be extracted from a plurality of host animals. The resultant antisera derived from the host animal or animals may be affinity purified to derive the antibodies 30 for use in the practice of the present invention. Such purification may be accomplished by any of a variety of techniques well-known in the art, such as via the use of separation column 15 whereby the antigenic peptides utilized to initiate the immune response are bound to a solid phase. According to conventional practice, the antisera may then be washed to remove antibodies not having specificity for the bound antigenic peptide or peptides which, as a consequence, allows the bound antibodies specific for the antigenic peptide or peptides to remain bound thereto, and ultimately eluted therefrom. The harvested antibodies may then be stored per conventional practices well-known to those skilled in the art.

As an alternative to deriving the desired antibodies from the antisera from one or more host animals, it is contemplated that monoclonal antibodies can be derived from antibody-producing cells obtained from the host animal. Utilizing techniques well-known in the art, such monoclonal antibodies may be derived by following the sequence of steps discussed above whereby a peptide antigen is administered to a host animal such as the host animal's immune system develops antibodies against the specific peptide antigen. Antibody producing white blood cells (i.e., B-cells) are then removed from the animal, typically via the animal's spleen, which are then fused with a tumor cell to form a hybridoma. Using well-known techniques, a hybridoma cell line is selected that secretes the desired monoclonal antibody that reacts strongly with particular antigenic peptides. Such cell line may then be utilized to produced large quantities of the monoclonal antibody utilizing methods well-known in the arts, such as growing such cell line in a host animal or using in vitro cell-culture techniques. In either case, as per the methodology discussed above, the hosted antibodies are stored per conventional practices.

Following the production and isolation of a first grouping of antibodies having a specificity for a first antigenic region of the FGF-23 molecule, the procedure depicted in FIG. 5 will be repeated utilizing a dissimilar antigenic peptide. In this regard, an antigenic peptide adhering to a different SEQ ID NO. will be utilized to thus enable a second grouping of antibodies to be formed that will be specific to a second dissimilar antigenic region present on the FGF-23 molecule. For example, to the extent the first group of antibodies is derived utilizing an antigenic peptide that is at least 70% identical to SEQ ID NOS. 4–5, the next grouping of antibodies will be derived using an antigenic peptide selected from the group consisting of SEQ ID NOS. 12–31. In this regard, in order to enable the sandwich-type immunoassay of the present invention to be properly practiced, the first and second antibodies must be derived such that the same have a specificity or affinity for separate and distinct antigenic regions present upon the FGF-23 molecule.

There has thus been provided immunoassays, assay methods, antibodies and methods of deriving antibodies that are directed to detecting FGF-23. As will be appreciated, additional modifications and improvements of the present invention may also be apparent to those of ordinary skill in the art. In this respect, once derivatized via the procedure set forth in FIG. 5, such antibodies may be used in immunological techniques to correlate the presence of FGF-23, as well as specific fragments thereof, as may be found in a given fluid biological sample. It will also be appreciated that the present invention may be utilized to derive antibodies for use in immunoassays that are applicable for a variety of species other than humans. For example, it is expressly contemplated that the immunoassays, assay methods, antibodies and methods of deriving antibodies of the present invention may be based upon mouse FGF-23, as referenced in FIG. 1a.

Thus, the particular combination of parts and steps described and illustrated herein is intended to represent only certain embodiments of the present invention, and is not intended to serve as limitations of alternative devices and methods within the spirit and scope of the invention.

What is claimed is:

1. A non-competitive immunoassay for detecting an FGF-23 protein molecule in a liquid sample suspected of containing molecules of FGF-23, wherein the FGF-23 protein molecule has an amino acid sequence selected from the group consisting of SEQ ID NO. 1 and SEQ ID NO. 2, said immtmoassay comprising the steps of:
   (1) contacting said liquid sample with
      (a) a first capture antibody, said first antibody having a specificity for a first amino acid sequence present upon the FGF-23 protein molecules wherein the first amino acid sequence includes at least one glycosylated amino acid residue therein,
      (b) a second antibody, said second antibody having a specificity for a second amino acid sequence present upon the FGF-23 protein molecule; wherein said specificity of said first antibody is dissimilar to said specificity of said second antibody such that in use, said first and second antibodies are capable of sequentially or simultaneously binding to an FGF-23 molecule; and
   (2) detecting complexes of said FGF-23 molecule bound to said first antibody and bound to said second antibody.

2. A non-competitive immunoassay for detecting an FGF-23 protein molecule in a liquid sample suspected of containing molecules of FGF-23, wherein the FGF-23 protein molecule has an amino acid sequence selected from the group consisting of SEQ ID NO. 1 and SEQ ID NO. 2, said immunoassay comprising the steps of:
   (1) contacting said liquid sample with
      (a) a first-capture antibody, said first antibody having a specificity for a first amino acid sequence present upon the FGF-23 protein molecule;
      (b) a second antibody, said second antibody having a specificity for a second amino acid sequence present upon the FGF-23 protein molecules wherein the second amino acid sequence includes at least one glycosylated amino acid residue therein; wherein said specificity of said first antibody is dissimilar to said specificity of said second antibody such that in use, said first and second antibodies are capable of sequentially or simultaneously binding to an FGF-23 molecule; and
   (2) detecting complexes of said FGF-23 molecule bound to said first antibody and bound to said second antibody.

3. A non-competitive immunoassay for detecting an FGF-23 protein molecule in a liquid sample suspected of containing molecules of FGF-23, wherein the FGF-23 protein molecule has an amino acid sequence selected from the group consisting of SEQ ID NO. 1 and SEQ ID NO. 2, said immunoassay comprising the steps of:
   (1) contacting said liquid sample with
      (a) a first capture antibody, said first antibody having a specificity for a first amino acid sequence selected from the group consisting of SEQ ID NO. 3, SEQ ID NO. 4, SEQ ID NO. 5, SEQ ID NO. 6, SEQ ID NO. 7, SEQ ID NO. 8, SEQ ID NO. 9, SEQ ID NO. 10, SEQ ID NO. 11, SEQ ID NO. 12, SEQ ID NO. 13, SEQ ID NO. 14, SEQ ID NO. 15, SEQ ID NO. 16, SEQ ID NO. 17, SEQ ID NO. 18, SEQ ID NO. 19, SEQ ID NO. 20, SEQ ID NO. 21, SEQ ID NO. 22, SEQ ID NO. 23, SEQ ID NO. 24, SEQ ID NO. 25, SEQ ID NO. 26, SEQ ID NO. 27, SEQ ID NO. 28, SEQ ID NO. 29, SEQ ID NO. 30, and SEQ ID NO. 31, wherein SEQ ID NO. 3, SEQ ID NO. 4, SEQ ID NO. 5, SEQ ID NO. 6, and SEQ ID NO. 7 have at least one glycosylated amino acid residue therein;
      (b) a second antibody, said second antibody having a specificity for a second amino acid sequence present upon the FGF-23 protein molecule; wherein said specificity of said first antibody is dissimilar to said specificity of said second antibody such that in use, said first and second antibodies are capable of sequentially or simultaneously binding to an FGF-23 molecule; and
   (2) detecting complexes of said FGF-23 molecule bound to said first antibody and bound to said second antibody.

4. A non-competitive immunoassay for detecting an FGF-23 protein molecule in a liquid sample suspected of containing molecules of FGF-23, wherein the FGF-23 protein molecule has an amino acid sequence selected from the group consisting of SEQ ID NO. 1 and SEQ ID NO. 2, said immunoassay comprising the steps of:
   (1) contacting said liquid sample with
      (a) a first capture antibody, said first antibody having a specificity for a first amino acid sequence present upon the FGF-23 protein molecules
      (b) a second antibody, said second antibody having a specificity for an amino acid sequence selected from the group consisting of SEQ ID NO. 3, SEQ ID NO. 4, SEQ ID NO. 5, SEQ ID NO. 6, SEQ ID NO. 7, SEQ ID NO. 8, SEQ ID NO. 9, SEQ ID NO. 10, SEQ ID NO. 11, SEQ ID NO. 12, SEQ ID NO. 13, SEQ ID NO. 14, SEQ ID NO. 15, SEQ ID NO. 16, SEQ ID NO. 17, SEQ ID NO. 18, SEQ ID NO. 19, SEQ ID NO. 20, SEQ ID NO. 21, SEQ ID NO. 22, SEQ ID NO. 23, SEQ ID NO. 24, SEQ ID NO. 25, SEQ ID NO. 26, SEQ ID NO. 27, SEQ ID NO. 28, SEQ ID NO. 29, SEQ ID NO. 30, and SEQ ID NO. 31, wherein SEQ ID NO. 3, SEQ ID NO. 4, SEQ ID NO. 5, SEQ ID NO. 6, and SEQ ID NO. 7 have at least one glycosylated amino acid residue therein; wherein said specificity of said first antibody is dissimilar to said specificity of said second antibody such that in use, said first and second antibodies are capable of sequentially or simultaneously binding to an FGF-23 molecule; and
   (2) detecting complexes of said FGF-23 molecule bound to said first antibody and bound to said second antibody.

5. A method of detecting the presence of FGF-23 protein molecules in a liquid sample, wherein the FGF-23 protein molecule has an amino acid sequence selected from the group consisting of SEQ ID NO. 1 and SEQ ID NO. 2, said method comprising the steps:
- (a) providing a capture first antibody, said first antibody having a specificity for a first antigenic amino acid sequence selected from the group consisting of SEQ ID NO. 3, SEQ ID NO. 4, SEQ ID NO. 5, SEQ ID NO. 6, SEQ ID NO. 7, SEQ ID NO. 8, SEQ ID NO. 9, SEQ ID NO. 10, SEQ ID NO. 11, SEQ ID NO. 12, SEQ ID NO. 13, SEQ ID NO. 14, SEQ ID NO. 15, SEQ ID NO. 16, SEQ ID NO. 17, SEQ ID NO. 18, SEQ ID NO. 19, SEQ ID NO. 20, SEQ ID NO. 21, SEQ ID NO. 22, SEQ ID NO. 23, SEQ ID NO. 24, SEQ ID NO. 25, SEQ ID NO. 26, SEQ ID NO. 27, SEQ ID NO. 28, SEQ ID NO. 29, SEQ ID NO. 30, and SEQ ID NO. 31, wherein SEQ ID Nos. 3 through 7 incorporate at least one glycosylated amino acid residue therein;
- (b) contacting said liquid sample with said first antibody such that said FGF-23 molecules become bound thereto;
- (c) providing a second antibody having a specificity for a second antigenic amino acid sequence formed upon the FGF-23 molecule, said second amino acid sequence being dissimilar from the sequence for which said first antibody in step a) is specific, said second antibody having a detectable moiety attached thereto; and
- (d) contacting said second antibody with said first antibody having said molecules of FGF-23 bound thereto such that said second antibody binds with said FGF-23 molecule; and
- (e) detecting the presence of FGF-23 via the detectable moiety attached to said second antibody.

6. A method of detecting the presence of FGF-23 protein molecules in a liquid sample, wherein the FGF-23 protein molecule has an amino acid sequence selected from the group consisting of SEQ ID NO. 1 and SEQ ID NO. 2, said method comprising the steps:
- (a) providing a capture first antibody, said first antibody having a specificity for a first amino acid sequence formed upon the FGF-23 molecule;
- (b) contacting said liquid sample with said first antibody such that said FGF-23 molecules become bound thereto;
- (c) providing a second antibody having a specificity for a second amino acid sequence selected from the group consisting of SEQ ID NO. 3, SEQ ID NO. 4, SEQ ID NO. 5, SEQ ID NO. 6, SEQ ID NO. 7, SEQ ID NO. 8, SEQ ID NO. 9, SEQ ID NO. 10, SEQ ID NO. 11, SEQ ID NO. 12, SEQ ID NO. 13, SEQ ID NO. 14, SEQ ID NO. 15, SEQ ID NO. 16, SEQ ID NO. 17, SEQ ID NO. 18, SEQ ID NO. 19, SEQ ID NO. 20, SEQ ID NO. 21, SEQ ID NO. 22, SEQ ID NO. 23, SEQ ID NO. 24, SEQ ID NO. 25, SEQ ID NO. 26, SEQ ID NO. 27, SEQ ID NO. 28, SEQ ID NO. 29, SEQ ID NO. 30, and SEQ ID NO. 31 wherein SEQ ID Nos. 3 through 7 incorporate at least one glycosylated amino acid residue therein, said second amino acid sequence being dissimilar from the sequence for which said first antibody in step a) is specific, said second antibody having a detectable moiety attached thereto; and
- (d) contacting said second antibody with said first antibody having said molecules of FGF-23 bound thereto such that said second antibody binds with said FGF-23 molecule; and
- (e) detecting the presence of FGF-23 via the detectable moiety attached to said second antibody.

7. A non-competitive immunoassay for detecting an FGF-23 protein molecule in a liquid sample suspected of containing-molecules of FGF-23, wherein the FGF-23 protein molecule has an amino acid sequence selected from the group consisting of SEQ ID NO. 1 and SEQ ID NO. 2, said immunoassay comprising the steps of:
- (1) contacting said liquid sample with
  - (a) a first capture antibody, said first antibody having a specificity for amino acid sequence SEQ ID NO. 24;
  - (b) a second antibody, said second antibody having a specificity for an amino acid sequence selected from the group consisting of SEQ ID NO. 9 and SEQ ID NO. 4; wherein said first and second antibodies are capable of sequentially or simultaneously binding to an FGF-23 molecule; and
- (2) detecting complexes of said FGF-23 molecule bound to said first antibody and bound to said second antibody.

8. A non-competitive immunoassay for detecting an FGF-23 protein molecule in a liquid sample suspected of containing molecules of FGF-23, wherein the FGF-23 protein molecule has an amino acid sequence selected from the group consisting of SEQ ID NO. 1 and SEQ ID NO. 2, said immunoassay comprising the steps of:
- (1) contacting said liquid sample with
  - (a) a first capture antibody, said first antibody having: a specificity for amino acid sequence SEQ ID NO. 28;
  - (b) a second antibody, said second antibody having a specificity for amino acid sequence SEQ ID NO. 24; wherein said first and second-antibodies are capable of sequentially or simultaneously binding to a molecule FGF-23; and
- (2) detecting complexes of said FGF-23 molecule bound to said first antibody and bound to said second antibody.

9. A method of detecting the presence of FGF-23 protein molecules in a liquid sample, wherein the FGF-23 protein molecule has an amino acid sequence selected from the group consisting of SEQ ID NO. 1 and SEQ ID NO. 2, said method comprising the steps:
- (a) providing a capture first antibody, said first antibody having a specificity for a first antigenic amino acid sequence SEQ ID NO. 24;
- (b) contacting said liquid sample with said first antibody such that said FGF-23 molecules become bound thereto;
- (c) providing a second antibody having a specificity for a second antigenic amino acid sequence selected from the group consisting of SEQ ID NO. 4 and SEQ ID NO. 9, said second antibody having a detectable moiety attached thereto; and
- (d) contacting said second antibody with said first antibody having said molecules of FGF-23 bound thereto such that said second antibody binds with said FGF-23 molecule; and
- (e) detecting the presence of FGF-23 via the detectable moiety attached to said second antibody.

10. A method of detecting the presence of FGF-23 protein molecules in a liquid sample, wherein the FGF-23 protein molecule has an amino acid sequence selected from the group consisting of SEQ ID NO. 1 and SEQ ID NO. 2, said method comprising the steps:
- (a) providing a capture first antibody, said first antibody having a specificity for a first amino acid sequence SEQ ID NO. 28;
- (b) contacting said liquid sample with said first antibody such that said FGF-23 molecules become bound thereto;
- (c) providing a second antibody having a specificity for a second amino acid sequence SEQ ID NO. 24, said second antibody having a detectable moiety attached thereto; and
- (d) contacting said second antibody with said first antibody having said molecules of FGF-23 bound thereto such that said second antibody binds with said FGF-23 molecule; and
- (e) detecting the presence of FGF-23 via the detectable moiety attached to said second antibody.

* * * * *

UNITED STATES PATENT AND TRADEMARK OFFICE
CERTIFICATE OF CORRECTION

| | | |
|---|---|---|
| PATENT NO. | : 7,094,551 B2 | Page 1 of 1 |
| APPLICATION NO. | : 10/245141 | |
| DATED | : August 22, 2006 | |
| INVENTOR(S) | : Richard J. Zahradnik, Jeffrey Lavigne and Harald Jueppner | |

It is certified that error appears in the above-identified patent and that said Letters Patent is hereby corrected as shown below:

Please delete the following shown in column 1, lines 8-10; under the heading STATEMENT RE: FEDERALLY SPONSORED RESEARCH/DEVELOPMENT "This invention was supported in part by a grant made by the United States government, and the United States government may have certain rights in the invention."

Please add -- (NA) -- in column 1 under the heading STATEMENT RE: FEDERALLY SPONSORED RESEARCH/DEVELOPMENT Signed and Sealed this Thirtieth Day of December, 2008

JON W. DUDAS
*Director of the United States Patent and Trademark Office*

SEQUENCE LISTING

```
<160> NUMBER OF SEQ ID NOS: 31

<210> SEQ ID NO 1
<211> LENGTH: 251
<212> TYPE: PRT
<213> ORGANISM: Human fibroblast growth factor-23 (FGF-23) peptide
      sequences

<400> SEQUENCE: 1

Met Leu Gly Ala Arg Leu Arg Leu Trp Val Cys Ala Leu Cys Ser Val
1               5                   10                  15

Cys Ser Met Ser Val Leu Arg Ala Tyr Pro Asn Ala Ser Pro Leu Leu
            20                  25                  30

Gly Ser Ser Trp Gly Gly Leu Ile His Leu Tyr Thr Ala Thr Ala Arg
        35                  40                  45

Asn Ser Tyr His Leu Gln Ile His Lys Asn Gly His Val Asp Gly Ala
    50                  55                  60

Pro His Gln Thr Ile Tyr Ser Ala Leu Met Ile Arg Ser Glu Asp Ala
65                  70                  75                  80

Gly Phe Val Val Ile Thr Gly Val Met Ser Arg Arg Tyr Leu Cys Met
                85                  90                  95

Asp Phe Arg Gly Asn Ile Phe Gly Ser His Tyr Phe Asp Pro Glu Asn
            100                 105                 110

Cys Arg Phe Gln His Gln Thr Leu Glu Asn Gly Tyr Asp Val Tyr His
        115                 120                 125

Ser Pro Gln Tyr His Phe Leu Val Ser Leu Gly Arg Ala Lys Arg Ala
    130                 135                 140
```

```
Phe Leu Pro Gly Met Asn Pro Pro Tyr Ser Gln Phe Leu Ser Arg
145                 150                 155                 160

Arg Asn Glu Ile Pro Leu Ile His Phe Asn Thr Pro Ile Pro Arg Arg
                165                 170                 175

His Thr Arg Ser Ala Glu Asp Asp Ser Glu Arg Asp Pro Leu Asn Val
            180                 185                 190

Leu Lys Pro Arg Ala Arg Met Thr Pro Ala Pro Ala Ser Cys Ser Gln
        195                 200                 205

Glu Leu Pro Ser Ala Glu Asp Asn Ser Pro Met Ala Ser Asp Pro Leu
    210                 215                 220

Gly Val Val Arg Gly Gly Arg Val Asn Thr His Ala Gly Gly Thr Gly
225                 230                 235                 240

Pro Glu Gly Cys Arg Pro Phe Ala Lys Phe Ile
                245                 250

<210> SEQ ID NO 2
<211> LENGTH: 251
<212> TYPE: PRT
<213> ORGANISM: Mouse fibroblast growth factor-23 peptide sequences

<400> SEQUENCE: 2

Met Leu Gly Thr Cys Leu Arg Leu Leu Val Gly Val Leu Cys Thr Val
1               5                   10                  15

Cys Ser Leu Gly Thr Ala Arg Ala Tyr Pro Asp Thr Ser Pro Leu Leu
                20                  25                  30

Gly Ser Asn Trp Gly Ser Leu Thr His Leu Tyr Thr Ala Thr Ala Arg
            35                  40                  45

Thr Ser Tyr His Leu Gln Ile His Arg Asp Gly His Val Asp Gly Thr
50                  55                  60

Pro His Gln Thr Ile Tyr Ser Ala Leu Met Ile Thr Ser Glu Asp Ala
65                  70                  75                  80

Gly Ser Val Val Ile Thr Gly Ala Met Thr Arg Arg Phe Leu Cys Met
                85                  90                  95

Asp Leu His Gly Asn Ile Phe Gly Ser Leu His Phe Ser Pro Glu Asn
            100                 105                 110

Cys Lys Phe Arg Gln Trp Thr Leu Glu Asn Gly Tyr Asp Val Tyr Leu
        115                 120                 125

Ser Gln Lys His His Tyr Leu Val Ser Leu Gly Arg Ala Lys Arg Ile
130                 135                 140

Phe Gln Pro Gly Thr Asn Pro Pro Phe Ser Gln Phe Leu Ala Arg
145                 150                 155                 160

Arg Asn Glu Val Pro Leu Leu His Phe Tyr Thr Val Arg Pro Arg Arg
                165                 170                 175

His Thr Arg Ser Ala Glu Asp Pro Glu Arg Asp Pro Leu Asn Val
            180                 185                 190

Leu Lys Pro Arg Pro Arg Ala Thr Pro Val Pro Val Ser Cys Ser Arg
        195                 200                 205

Glu Leu Pro Ser Ala Glu Glu Gly Pro Ala Ala Ser Asp Pro Leu
    210                 215                 220

Gly Val Leu Arg Arg Gly Arg Gly Asp Ala Arg Gly Gly Ala Gly Gly
225                 230                 235                 240

Ala Asp Arg Cys Arg Pro Phe Pro Arg Phe Val
                245                 250

<210> SEQ ID NO 3
```

```
<211> LENGTH: 227
<212> TYPE: PRT
<213> ORGANISM: Human FGF-23 residues 25-251

<400> SEQUENCE: 3

Tyr Pro Asn Ala Ser Pro Leu Leu Gly Ser Ser Trp Gly Gly Leu Ile
1               5                   10                  15

His Leu Tyr Thr Ala Thr Ala Arg Asn Ser Tyr His Leu Gln Ile His
            20                  25                  30

Lys Asn Gly His Val Asp Gly Ala Pro His Gln Thr Ile Tyr Ser Ala
        35                  40                  45

Leu Met Ile Arg Ser Glu Asp Ala Gly Phe Val Val Ile Thr Gly Val
    50                  55                  60

Met Ser Arg Arg Tyr Leu Cys Met Asp Phe Arg Gly Asn Ile Phe Gly
65                  70                  75                  80

Ser His Tyr Phe Asp Pro Glu Asn Cys Arg Phe Gln His Gln Thr Leu
                85                  90                  95

Glu Asn Gly Tyr Asp Val Tyr His Ser Pro Gln Tyr His Phe Leu Val
            100                 105                 110

Ser Leu Gly Arg Ala Lys Arg Ala Phe Leu Pro Gly Met Asn Pro Pro
        115                 120                 125

Pro Tyr Ser Gln Phe Leu Ser Arg Arg Asn Glu Ile Pro Leu Ile His
    130                 135                 140

Phe Asn Thr Pro Ile Pro Arg Arg His Thr Arg Ser Ala Glu Asp Asp
145                 150                 155                 160

Ser Glu Arg Asp Pro Leu Asn Val Leu Lys Pro Arg Ala Arg Met Thr
                165                 170                 175

Pro Ala Pro Ala Ser Cys Ser Gln Glu Leu Pro Ser Ala Glu Asp Asn
            180                 185                 190

Ser Pro Met Ala Ser Asp Pro Leu Gly Val Val Arg Gly Gly Arg Val
        195                 200                 205

Asn Thr His Ala Gly Gly Thr Gly Pro Glu Gly Cys Arg Pro Phe Ala
    210                 215                 220

Lys Phe Ile
225

<210> SEQ ID NO 4
<211> LENGTH: 18
<212> TYPE: PRT
<213> ORGANISM: Human FGF-23 residues 25-42

<400> SEQUENCE: 4

Tyr Pro Asn Ala Ser Pro Leu Leu Gly Ser Ser Trp Gly Gly Leu Ile
1               5                   10                  15

His Leu

<210> SEQ ID NO 5
<211> LENGTH: 45
<212> TYPE: PRT
<213> ORGANISM: Human FGF-23 residues 25-69

<400> SEQUENCE: 5

Tyr Pro Asn Ala Ser Pro Leu Leu Gly Ser Ser Trp Gly Gly Leu Ile
1               5                   10                  15

His Leu Tyr Thr Ala Thr Ala Arg Asn Ser Tyr His Leu Gln Ile His
            20                  25                  30

Lys Asn Gly His Val Asp Gly Ala Pro His Gln Thr Ile
```

<210> SEQ ID NO 6
<211> LENGTH: 76
<212> TYPE: PRT
<213> ORGANISM: Human FGF-23 residues 25-100

<400> SEQUENCE: 6

Tyr Pro Asn Ala Ser Pro Leu Leu Gly Ser Ser Trp Gly Gly Leu Ile
1               5                   10                  15

His Leu Tyr Thr Ala Thr Ala Arg Asn Ser Tyr His Leu Gln Ile His
            20                  25                  30

Lys Asn Gly His Val Asp Gly Ala Pro His Gln Thr Ile Tyr Ser Ala
        35                  40                  45

Leu Met Ile Arg Ser Glu Asp Ala Gly Phe Val Val Ile Thr Gly Val
    50                  55                  60

Met Ser Arg Arg Tyr Leu Cys Met Asp Phe Arg Gly
65                  70                  75

<210> SEQ ID NO 7
<211> LENGTH: 150
<212> TYPE: PRT
<213> ORGANISM: Human FGF-23 residues 25-174

<400> SEQUENCE: 7

Tyr Pro Asn Ala Ser Pro Leu Leu Gly Ser Ser Trp Gly Gly Leu Ile
1               5                   10                  15

His Leu Tyr Thr Ala Thr Ala Arg Asn Ser Tyr His Leu Gln Ile His
            20                  25                  30

Lys Asn Gly His Val Asp Gly Ala Pro His Gln Thr Ile Tyr Ser Ala
        35                  40                  45

Leu Met Ile Arg Ser Glu Asp Ala Gly Phe Val Val Ile Thr Gly Val
    50                  55                  60

Met Ser Arg Arg Tyr Leu Cys Met Asp Phe Arg Gly Asn Ile Phe Gly
65                  70                  75                  80

Ser His Tyr Phe Asp Pro Glu Asn Cys Arg Phe Gln His Gln Thr Leu
                85                  90                  95

Glu Asn Gly Tyr Asp Val Tyr His Ser Pro Gln Tyr His Phe Leu Val
            100                 105                 110

Ser Leu Gly Arg Ala Lys Arg Ala Phe Leu Pro Gly Met Asn Pro Pro
        115                 120                 125

Pro Tyr Ser Gln Phe Leu Ser Arg Arg Asn Glu Ile Pro Leu Ile His
    130                 135                 140

Phe Asn Thr Pro Ile Pro
145                 150

<210> SEQ ID NO 8
<211> LENGTH: 16
<212> TYPE: PRT
<213> ORGANISM: Human FGF-23 residues 41-56

<400> SEQUENCE: 8

His Leu Tyr Thr Ala Thr Ala Arg Asn Ser Tyr His Leu Gln Ile His
1               5                   10                  15

<210> SEQ ID NO 9
<211> LENGTH: 19
<212> TYPE: PRT
<213> ORGANISM: Human FGF-23 residues 51-69

```
<400> SEQUENCE: 9

Tyr His Leu Gln Ile His Lys Asn Gly His Val Asp Gly Ala Pro His
1               5                   10                  15

Gln Thr Ile

<210> SEQ ID NO 10
<211> LENGTH: 24
<212> TYPE: PRT
<213> ORGANISM: Human FGF-23 residues 58-81

<400> SEQUENCE: 10

Asn Gly His Val Asp Gly Ala Pro His Gln Thr Ile Tyr Ser Ala Leu
1               5                   10                  15

Met Ile Arg Ser Glu Asp Ala Gly
            20

<210> SEQ ID NO 11
<211> LENGTH: 17
<212> TYPE: PRT
<213> ORGANISM: Human FGF-23 residues 65-81

<400> SEQUENCE: 11

Pro His Gln Thr Ile Tyr Ser Ala Leu Met Ile Arg Ser Glu Asp Ala
1               5                   10                  15

Gly

<210> SEQ ID NO 12
<211> LENGTH: 16
<212> TYPE: PRT
<213> ORGANISM: Human FGF-23 residues 70-85

<400> SEQUENCE: 12

Tyr Ser Ala Leu Met Ile Arg Ser Glu Asp Ala Gly Phe Val Val Ile
1               5                   10                  15

<210> SEQ ID NO 13
<211> LENGTH: 17
<212> TYPE: PRT
<213> ORGANISM: Human FGF-23 residues 84-100

<400> SEQUENCE: 13

Val Ile Thr Gly Val Met Ser Arg Arg Tyr Leu Cys Met Asp Phe Arg
1               5                   10                  15

Gly

<210> SEQ ID NO 14
<211> LENGTH: 26
<212> TYPE: PRT
<213> ORGANISM: Human FGF-23 residues 90-115

<400> SEQUENCE: 14

Ser Arg Arg Tyr Leu Cys Met Asp Phe Arg Gly Asn Ile Phe Gly Ser
1               5                   10                  15

His Tyr Phe Asp Pro Glu Asn Cys Arg Phe
            20                  25

<210> SEQ ID NO 15
<211> LENGTH: 21
<212> TYPE: PRT
<213> ORGANISM: Human FGF-23 residues 100-120
```

-continued

```
<400> SEQUENCE: 15

Gly Asn Ile Phe Gly Ser His Tyr Phe Asp Pro Glu Asn Cys Arg Phe
1               5                   10                  15

Gln His Gln Thr Leu
            20

<210> SEQ ID NO 16
<211> LENGTH: 21
<212> TYPE: PRT
<213> ORGANISM: Human FGF-23 residues 110-130

<400> SEQUENCE: 16

Pro Glu Asn Cys Arg Phe Gln His Gln Thr Leu Glu Asn Gly Tyr Asp
1               5                   10                  15

Val Tyr His Ser Pro
            20

<210> SEQ ID NO 17
<211> LENGTH: 11
<212> TYPE: PRT
<213> ORGANISM: Human FGF-23 residues 119-129

<400> SEQUENCE: 17

Thr Leu Glu Asn Gly Tyr Asp Val Tyr His Ser
1               5                   10

<210> SEQ ID NO 18
<211> LENGTH: 21
<212> TYPE: PRT
<213> ORGANISM: Human FGF-23 residues 130-150

<400> SEQUENCE: 18

Pro Gln Tyr His Phe Leu Val Ser Leu Gly Arg Ala Lys Arg Ala Phe
1               5                   10                  15

Leu Pro Gly Met Asn
            20

<210> SEQ ID NO 19
<211> LENGTH: 21
<212> TYPE: PRT
<213> ORGANISM: Human FGF-23 residues 140-160

<400> SEQUENCE: 19

Arg Ala Lys Arg Ala Phe Leu Pro Gly Met Asn Pro Pro Pro Tyr Ser
1               5                   10                  15

Gln Phe Leu Ser Arg
            20

<210> SEQ ID NO 20
<211> LENGTH: 21
<212> TYPE: PRT
<213> ORGANISM: Human FGF-23 residues 150-170

<400> SEQUENCE: 20

Asn Pro Pro Pro Tyr Ser Gln Phe Leu Ser Arg Arg Asn Glu Ile Pro
1               5                   10                  15

Leu Ile His Phe Asn
            20

<210> SEQ ID NO 21
<211> LENGTH: 15
<212> TYPE: PRT
```

-continued

<213> ORGANISM: Human FGF-23 residues 160-174

<400> SEQUENCE: 21

Arg Arg Asn Glu Ile Pro Leu Ile His Phe Asn Thr Pro Ile Pro
1               5                   10                  15

<210> SEQ ID NO 22
<211> LENGTH: 72
<212> TYPE: PRT
<213> ORGANISM: Human FGF-23 residues 180-251

<400> SEQUENCE: 22

Ser Ala Glu Asp Asp Ser Glu Arg Asp Pro Leu Asn Val Leu Lys Pro
1               5                   10                  15
Arg Ala Arg Met Thr Pro Ala Pro Ala Ser Cys Ser Gln Glu Leu Pro
            20                  25                  30
Ser Ala Glu Asp Asn Ser Pro Met Ala Ser Asp Pro Leu Gly Val Val
        35                  40                  45
Arg Gly Gly Arg Val Asn Thr His Ala Gly Gly Thr Gly Pro Glu Gly
    50                  55                  60
Cys Arg Pro Phe Ala Lys Phe Ile
65                  70

<210> SEQ ID NO 23
<211> LENGTH: 27
<212> TYPE: PRT
<213> ORGANISM: Human FGF-23 residues 180-206

<400> SEQUENCE: 23

Ser Ala Glu Asp Asp Ser Glu Arg Asp Pro Leu Asn Val Leu Lys Pro
1               5                   10                  15
Arg Ala Arg Met Thr Pro Ala Pro Ala Ser Cys
            20                  25

<210> SEQ ID NO 24
<211> LENGTH: 21
<212> TYPE: PRT
<213> ORGANISM: Human FGF-23 residues 186-206

<400> SEQUENCE: 24

Glu Arg Asp Pro Leu Asn Val Leu Lys Pro Arg Ala Arg Met Thr Pro
1               5                   10                  15
Ala Pro Ala Ser Cys
            20

<210> SEQ ID NO 25
<211> LENGTH: 59
<212> TYPE: PRT
<213> ORGANISM: Human FGF-23 residues 186-244

<400> SEQUENCE: 25

Glu Arg Asp Pro Leu Asn Val Leu Lys Pro Arg Ala Arg Met Thr Pro
1               5                   10                  15
Ala Pro Ala Ser Cys Ser Gln Glu Leu Pro Ser Ala Glu Asp Asn Ser
            20                  25                  30
Pro Met Ala Ser Asp Pro Leu Gly Val Val Arg Gly Gly Arg Val Asn
        35                  40                  45
Thr His Ala Gly Gly Thr Gly Pro Glu Gly Cys
    50                  55

<210> SEQ ID NO 26
<211> LENGTH: 17
<212> TYPE: PRT
<213> ORGANISM: Human FGF-23 residues 206-222

<400> SEQUENCE: 26

Cys Ser Gln Glu Leu Pro Ser Ala Glu Asp Asn Ser Pro Met Ala Ser
1               5                   10                  15

Asp

<210> SEQ ID NO 27
<211> LENGTH: 39
<212> TYPE: PRT
<213> ORGANISM: Human FGF-23 residues 206-244

<400> SEQUENCE: 27

Cys Ser Gln Glu Leu Pro Ser Ala Glu Asp Asn Ser Pro Met Ala Ser
1               5                   10                  15

Asp Pro Leu Gly Val Val Arg Gly Gly Arg Val Asn Thr His Ala Gly
            20                  25                  30

Gly Thr Gly Pro Glu Gly Cys
        35

<210> SEQ ID NO 28
<211> LENGTH: 20
<212> TYPE: PRT
<213> ORGANISM: Human FGF-23 residues 225-244

<400> SEQUENCE: 28

Gly Val Val Arg Gly Gly Arg Val Asn Thr His Ala Gly Gly Thr Gly
1               5                   10                  15

Pro Glu Gly Cys
            20

<210> SEQ ID NO 29
<211> LENGTH: 27
<212> TYPE: PRT
<213> ORGANISM: Human FGF-23 residues 225-251

<400> SEQUENCE: 29

Gly Val Val Arg Gly Gly Arg Val Asn Thr His Ala Gly Gly Thr Gly
1               5                   10                  15

Pro Glu Gly Cys Arg Pro Phe Ala Lys Phe Ile
            20                  25

<210> SEQ ID NO 30
<211> LENGTH: 22
<212> TYPE: PRT
<213> ORGANISM: Human FGF-23 residues 230-251

<400> SEQUENCE: 30

Gly Arg Val Asn Thr His Ala Gly Gly Thr Gly Pro Glu Gly Cys Arg
1               5                   10                  15

Pro Phe Ala Lys Phe Ile
            20

<210> SEQ ID NO 31
<211> LENGTH: 12
<212> TYPE: PRT
<213> ORGANISM: Human FGF-23 residues 240-251

-continued

```
<400> SEQUENCE: 31

Gly Pro Glu Gly Cys Arg Pro Phe Ala Lys Phe Ile
1               5                   10
```